US010709827B2

(12) United States Patent
Janeczek et al.

(10) Patent No.: US 10,709,827 B2
(45) Date of Patent: Jul. 14, 2020

(54) MEMBRANE CATHETER

(71) Applicant: TECHNISCHE UNIVERSITÄT WIEN, Vienna (AT)

(72) Inventors: Christoph Janeczek, Felixdorf (AT); Margit Gföhler, Vienna (AT); Michael Harasek, Vienna (AT)

(73) Assignee: TECHNISCHE UNIVERSITÄT WIEN, Vienna (AT)

( * ) Notice: Subject to any disclaimer, the term of this patent is extended or adjusted under 35 U.S.C. 154(b) by 280 days.

(21) Appl. No.: 15/950,218

(22) Filed: Apr. 11, 2018

(65) Prior Publication Data

US 2018/0228950 A1   Aug. 16, 2018

Related U.S. Application Data

(63) Continuation-in-part of application No. PCT/EP2016/074776, filed on Oct. 14, 2016.

(30) Foreign Application Priority Data

Oct. 14, 2015 (EP) .................................... 15189777
Apr. 20, 2017 (AT) .............................. A 50318/2017

(51) Int. Cl.
*A61M 1/10* (2006.01)
*A61M 1/16* (2006.01)
(Continued)

(52) U.S. Cl.
CPC .......... *A61M 1/1006* (2014.02); *A61M 1/125* (2014.02); *A61M 1/1678* (2013.01);
(Continued)

(58) Field of Classification Search
CPC .... A61M 1/1006; A61M 1/10; A61M 1/1005; A61M 1/1008; A61M 1/101;
(Continued)

(56) References Cited

U.S. PATENT DOCUMENTS 4,631,053 A   12/1986   Taheri
8,641,659 B2 *  2/2014   Soykan ................. A61M 1/284
                                                              604/27
(Continued)

FOREIGN PATENT DOCUMENTS

DE   10 2006 036 948   2/2008
GB        2004092      3/1979
(Continued)

OTHER PUBLICATIONS

International Search Report dated Dec. 23, 2016 issued in PCT International Patent Application No. PCT/EP2016/074776, 10 pp.
(Continued)

*Primary Examiner* — Philip R Wiest
(74) *Attorney, Agent, or Firm* — Nixon & Vanderhye P.C.

(57) ABSTRACT

A substance exchange device for intracorporal use includes a cavity for receiving blood having at least one blood inlet and at least one blood outlet, a substance exchange membrane adjoining the cavity, a supply duct for supplying an exchange fluid to the substance exchange membrane, a blood pump arranged within the cavity and a drive unit for the blood pump. The blood pump is configured to pump blood in a direction from a blood inlet to a blood outlet of the cavity. The drive unit includes a turbine, which is connected to the supply duct and may be driven by an exchange fluid supplied via the supply duct, where the turbine includes at least a rotor coupled to the blood pump and a stator (turbine nozzle) arranged upstream of the rotor.

17 Claims, 7 Drawing Sheets

(51) Int. Cl.
*A61M 1/12* (2006.01)
*A61M 1/36* (2006.01)

(52) U.S. Cl.
CPC ........... *A61M 1/1698* (2013.01); *A61M 1/101* (2013.01); *A61M 1/1008* (2014.02); *A61M 1/1013* (2014.02); *A61M 1/1025* (2014.02); *A61M 1/1036* (2014.02); *A61M 1/3659* (2014.02); *A61M 2205/3317* (2013.01); *A61M 2205/3365* (2013.01); *A61M 2206/14* (2013.01); *A61M 2206/20* (2013.01)

(58) Field of Classification Search
CPC .............. A61M 1/1013; A61M 1/1015; A61M 1/1025; A61M 1/1032; A61M 1/1036; A61M 1/125; A61M 1/1678; A61M 1/3659; A61M 1/3672; A61B 5/14525; A61B 5/14532; A61B 5/6852
See application file for complete search history.

(56) References Cited

U.S. PATENT DOCUMENTS

| | | | |
|---|---|---|---|
| 9,446,179 B2 | 9/2016 | Keenan | |
| 2009/0254022 A1* | 10/2009 | Cattaneo | A61M 1/1625 604/26 |
| 2010/0258116 A1* | 10/2010 | Federspiel | B01D 53/229 128/200.25 |
| 2013/0053623 A1* | 2/2013 | Evans | A61M 1/101 600/16 |
| 2014/0010686 A1* | 1/2014 | Tanner | A61M 1/1036 417/420 |
| 2014/0275726 A1* | 9/2014 | Zeng | A61M 1/1012 600/16 |
| 2016/0000983 A1* | 1/2016 | Mohl | A61M 1/1086 600/17 |
| 2017/0080136 A1* | 3/2017 | Janeczek | H02K 49/108 |
| 2018/0228950 A1 | 8/2018 | Janeczek | |

FOREIGN PATENT DOCUMENTS

| | | |
|---|---|---|
| GB | 2505068 | 2/2014 |
| WO | WO 03/061727 | 7/2003 |
| WO | WO 2004/016300 | 2/2004 |
| WO | WO 2006/031858 | 3/2006 |
| WO | WO 2008/046630 | 4/2008 |
| WO | WO 2015/172173 | 11/2015 |

OTHER PUBLICATIONS

Austrian Office Action dated Nov. 14, 2017 issued in Austrian Patent Application No. A 50318/2017, 3 pp.
European Search Report dated Mar. 22, 2016 issued in European Patent Application No. 15189777.4, 10 pp.
U.S. Office Action dated Apr. 16, 2020 issued in U.S. Appl. No. 15/768,705, 13 pp.

* cited by examiner

MEMBRANE CATHETER

CROSS-REFERENCES TO RELATED APPLICATIONS

This application is a continuation-in-part (CIP) of PCT International Patent Application No. PCT/EP2016/074776, filed Oct. 14, 2016, pending, which designated the U.S. and claims priority to European Patent Application No. 15189777.4, filed Oct. 14, 2015, the entire contents of each of which are hereby incorporated by reference in this application. This application also claims priority to Austrian Patent Application No. A 50318/2017, filed on Apr. 20, 2017, the entire contents of which is hereby incorporated by reference in this application

STATEMENT REGARDING FEDERALLY SPONSORED RESEARCH OR DEVELOPMENT (NOT APPLICABLE)

BACKGROUND OF THE INVENTION

The invention relates to a substance exchange device for intracorporeal use, comprising a cavity for receiving blood having at least one blood inlet and at least one blood outlet, a substance exchange membrane adjoining the cavity, a supply duct for supplying an exchange fluid to the substance exchange membrane, a blood pump arranged within the cavity and a drive unit for the blood pump, wherein the blood pump is configured to pump blood in a direction from the blood inlet to the blood outlet of the cavity.

In this context, a substance exchange device is any device for exchanging substances from blood or into blood. The substance exchange membrane may have a first side and a second side opposite the first side, wherein the first side may adjoin the cavity and wherein the supply duct may be configured to supply the exchange fluid to the second side of the substance exchange membrane. An exchange substance contained in or corresponding to the exchange fluid may pass over the membrane into the blood on the other side or, the other way round, an exchange substance may pass from the blood into the exchange fluid. During operation the blood pump may be used to create a local pressure difference between the blood inlet and the blood outlet to enable the required blood flow via the membrane. Otherwise, there would hardly be any blood flow via the membrane due to its flow resistance. By virtue of the blood pump, the pressure loss caused by the substance exchange device is compensated at least in part. In particular, the blood pump may enable the blood flow via the membrane and increase it along the substance exchange device, and optionally the blood flow may be supported by a bypass arranged upstream of the membrane.

The blood pump may be any conveying device which is configured to at least partially compensate for a pressure difference between the blood inlet and the blood outlet during operation. The conveying device may comprise a drive unit for generating a torque and a pump rotor connected with the drive unit for the transmission of a torque. For example, the drive unit may comprise an electric motor. That achieves a simple control of the conveying device, in particular of the rotational speed of the rotor.

Substance exchange devices, such as intravascular membrane oxygenators, are known from patent documents in different embodiment variations. For example, WO 2004/016300 A2 discloses an intravenous oxygenator configured as a catheter for oxygenating the blood, having a membrane in the form of a fibre bundle, with each of the fibres connected to a gas supply via a first port and to a gas exhaust via a second port. The fibre bundle is torsion-bent by a relative twisting of the first port of the fibres with respect to the second port of the fibres around the longitudinal axis of the oxygenator during operation. As a consequence, the fibres extend along the entire length of the fibre bundle as continuous gas conduits. During operation of the oxygenator, oxygen is supplied, flowing into the fibres via the first port and causing a diffuse gas exchange with blood on the surface of the fibres. During this, the blood is enriched with oxygen while $CO_2$ is being removed at the same time. Consequently, a gas mixture of oxygen and carbon dioxide is present in the fibres at the second port, which mixture flows through an exhaust chamber in a tube and out of the patient's body through the tube. The blood flowing into the oxygenator passes through the torsion-bent fibre bundle and reaches a pump. Here, the blood is conveyed in the flow direction of the vein and leaves the oxygenator through an outlet. Thus, the pressure drop of the blood is compensated for by the pump, so the pressure at the outlet equals the physiological pressure again.

Only marginally, US 2010/258116 A1 mentions the use of a rotor, but without any indication of its use as a blood pump. The impeller is not presented in more detail and no executable technical solution on how to possibly arrange and drive such a rotor is given, so the function of the impeller remains unclear.

The pump shown in US 2013/053623 A1 serves to support the cardiac function and thus relates to an entirely different field of application than the present device. Naturally, the pump shown does not comprise a membrane as defined by the device according to the invention, i.e., for the exchange of substances.

In the device shown in GB 2505068 A, a blood pump is driven by a drive shaft of a drive unit located outside the body. This means that in this case the drive unit is not a part of the substance exchange device for intracorporeal use.

BRIEF SUMMARY OF THE INVENTION

It is an object of the invention to avoid a separate power supply of the drive unit.

This object is achieved according to the invention by a substance exchange device of the initially presented type in such a way that the drive unit comprises a turbine, which is connected to the supply duct and may be driven by an exchange fluid supplied via the supply duct, wherein the turbine comprises at least a rotor coupled to the blood pump and a stator (turbine nozzle)

Preferably, the stator of the turbine is arranged upstream of the rotor of the turbine. This means that the stator (turbine nozzle) is arranged upstream of the rotor with respect to the flow direction of the exchange fluid during operation. The turbine element may form part of a general drive unit. The exchange fluid or carrier medium may flow around the turbine element during operation. The stator (turbine nozzle) arranged upstream of the rotor provides for a correct approaching flow to the turbine's rotor by the exchange fluid flowing (such as an exchange substance or a carrier medium) through the stator (turbine nozzle).

A part of the internal energy of the flowing exchange fluid is converted to mechanical power by the turbine and delivered to the blood pump by a shaft. The exchange fluid may be liquid or gaseous. It may be supplied to the substance exchange device from outside of the body by means of a catheter and be conveyed through the substance exchange device by an extracorporeal pump. The exchange fluid may be a liquid or gaseous exchange substance, or a liquid or gaseous carrier medium or conveying medium in which the exchange substance is present in solution and/or with which the exchange substance is mixed and/or by which the exchange substance is taken in from the blood.

An object of the drive unit is the conversion of energy supplied by the fluid to a torque within the substance exchange device, which torque is transmitted to a shaft. In this way, the power supply of the drive unit is obtained together with the supply of the exchange fluid and not separately and/or independently thereof. In particular, no electrical connection of the drive unit from outside of the body is required. This means that both the blood pump and the turbine are integrated into the substance exchange device. The axis of the shaft is arranged substantially parallel to a longitudinal extension axis of the substance exchange device. The shaft transmits the torque created in the drive unit to a pump rotor of the blood pump, which pump rotor is connected to the drive unit. Eventually, the pump rotor transmits the torque to the blood. In such a conveying device, comprising a turbine as the drive unit and a blood pump as the working machine, a part of the flow energy of the exchange fluid is transmitted to the conveyed blood.

In addition to the supply duct the substance exchange device may comprise a return duct for returning the exchange fluid from the substance exchange membrane. The present invention is not limited to one of each of a supply duct and a return duct. In particular, two supply ducts and/or two return ducts may be provided, for example with different supply ducts and/or different return ducts being connected to the membrane and the turbine, respectively. This makes it possible to obtain an independent control of the substance exchange membrane and the turbine. In particular, in this case the systems turbine and substance exchange membrane may be controlled independently of each other even when possible controlled valves are not located within the body but arranged within an external control unit.

Connected to an extracorporeal conveying and exchange assembly for reprocessing and conveying of the exchange fluid, the substance exchange device may be dimensioned as a complete system using components already present in the market such that it is portable and the extracorporeal circuit with or at the console may even be carried in a bag.

A torque is preferably transmitted from the drive unit to the pump rotor along a shaft the axis of which is arranged substantially in parallel to a longitudinal axis of extension of the substance exchange device (e.g. a catheter). In the simplest and most reliable case, the turbine element is coupled directly to the pump rotor, so both elements operate at the same speed during use. Even in case of an indirect coupling, for example via a magnetic coupling (see below), the blood pump and the turbine may be operated at the same speed, for example by using the same number of magnet pole pairs in the coupling. By adapting the blood pump and the turbine to a desired operating point (speed, pressure conditions, volumetric flows), an optimised operation of the substance exchange device may be obtained in both cases.

It is favourable for a pump rotor of the blood pump to be supported in a sliding contact bearing. In this case, the blood itself is used as the lubricant. This advantage may be obtained independently of the arrangement of the rotor and the stator of the turbine.

Furthermore, a pump rotor and other parts of the blood pump may be made of technical ceramics such as alumina, a metal such as titanium or a plastic material such as PEEK (poly-ether ether ketone) and, preferably, be provided with a surface coating as well. These materials are particularly suited for use in the blood circuit.

Moreover, it is advantageous to integrate at least one speed sensor in the substance exchange device, which speed sensor is configured to sense the speed of the turbine, the blood pump or a coupling between the blood pump and the turbine. In this context, integrated means that the speed sensor is a part of the substance exchange device and is thus located intracorporeally during operation of the substance exchange device. Multiple speed sensors may be provided for sensing the speed at several of the mentioned locations. The sensed speed may then be converted to an electronic signal and be used to monitor and check the proper operation of the substance exchange device. In particular, a Hall sensor may be provided as the speed sensor.

In an embodiment of the present invention the blood pump may be coupled to the turbine via a gearing, which gearing is configured to reduce the speed of the blood pump with respect to the speed of the turbine. Such a reduction is particularly advantageous when using a gaseous exchange fluid, so the turbine can be operated at a correspondingly higher speed than required for the blood pump. In general, an operating point of the turbine suited for the respective exchange fluid at a specified speed of the blood pump may be obtained with the aid of the gearing.

Furthermore, it has proven favourable for the present substance exchange device to comprise one or more return duct(s) for returning an exchange fluid from the substance exchange membrane and/or the turbine, wherein the return duct is configured to withstand a negative pressure (i.e., a negative differential pressure with respect to an ambient pressure of approx. 1 bar). In this case, the overpressure of the supply duct may be reduced or avoided in its entirety, so the risk of exchange fluid escaping into the blood in case of leakage may be reduced. By applying a vacuum instead of the exchange fluid, a concentration gradient at the substance exchange membrane may be obtained as well.

In conjunction with the drive unit it is favourable for the pump rotor to be connected to the drive unit via a magnetic coupling, wherein the magnetic coupling comprises two coupling parts for torque transmission along an axis of rotation, said coupling parts being rotatable relative to each other and each having a permanent magnet. For example, a concentric ring coupling or a disc coupling may be used as the magnetic coupling. Compared to a continuous mechanical connection, for example in the form of a continuous shaft, a magnetic coupling has the advantage that the transmitted torque is limited and a hermetic separation between blood-carrying and non-blood-carrying parts may be established. While the pump rotor also stops in case of the turbine getting stuck, the limitation is technically reasonable nevertheless since failure can be detected. Should the turbine rev up due to a fault, the magnetic coupling would cease transmitting the power at some point in time. This protects the blood circuit from overloading.

In order to be able to transmit a desired torque with a particularly compact magnetic coupling as well, it has been proven advantageous for one of the coupling parts to comprise an at least partially ferromagnetic guiding element which is non-rotatably connected to the permanent magnet of the coupling part, wherein one part of the guiding element is disposed radially outside of the permanent magnet of the other coupling part. Such a magnetic coupling is shown in WO 2015/172173 A2, for example, the content of which is incorporated in this application herewith. This means that the magnetic coupling comprises two coupling parts which can be rotated relative to each other, wherein a drive-side coupling part comprises a drive-side permanent magnet and an output-side coupling part comprises an output-side permanent magnet that lies opposite and at a distance from the drive-side permanent magnet along the axis of rotation, wherein one of the coupling parts comprises an at least partially ferromagnetic guiding element which is non-rotatably connected to the permanent magnet of the coupling part, wherein one part of the guiding element is disposed radially outside of the opposite permanent magnet. With respect to traditional concentric ring couplings, this design has the advantage that it may be produced in a simpler and more economical way and requires a smaller total coupling area since a part of the torque is transmitted via the front side of the coupling parts. With respect to traditional disc couplings, it has the advantage that smaller radial dimensions are required for transmitting a certain torque. Comparable to the outer coupling part of a concentric ring coupling, the guiding element may be shaped as a cup or a hollow cylinder and may surround the respective other coupling part circumferentially, i.e., preferably it extends radially outside of both permanent magnets. The guiding element may be formed as a thin-walled hollow cylinder, for example, so that with unchanged dimensions the magnetised volume of the disc coupling is retained to the greatest possible extent and, at the same time, a transmittable torque comparable to that of a concentric ring coupling may be obtained between the guiding element and the opposite permanent magnet at a distance therefrom. The direction of magnetisation of the permanent magnets is preferably oriented perpendicular to the axis of rotation, i.e., the poles of the magnets extend circumferentially from south to north and are—at least in a two-pole design—diametrically opposite each other with respect to the axis of rotation. By means of the guiding element, magnetic field lines extending radially from the permanent magnets are bundled, and due to the ferromagnetic material of the guiding element the magnetic force between the coupling parts is further increased. The magnetic force for transmitting the torque is raised by compressing the magnetic field lines in the ferromagnetic material. Advantageously, due to the larger volumes of the permanent magnets when compared to concentric ring couplings with equal dimensions of the couplings, a shorter axial extension and thus lower radial transverse forces on the bearings of the coupling parts can be achieved.

The permanent magnets of the magnetic coupling may each be 2-, 4- or 6-pole permanent magnets. Preferably they are two-pole permanent magnets with each having two half-cylindrical magnetic poles. The at least partially ferromagnetic guiding element may comprise at least one diamagnetic or paramagnetic separation. This separation parts the guiding element into at least two ferromagnetic sections and thus avoids magnetic short circuits. A diamagnetic separation or a para-magnetic separation (made of aluminum or brass, for example) may be used. Paramagnetic refers to materials having a magnetic permeability of just slightly above 1, in particular having a magnetic permeability below 1.2, preferably having a magnetic permeability below 1.05.

In addition to the radially outside arrangement the guiding element may also extend at a rear side of the non-rotatably connected permanent magnet, which rear side is facing away from the opposite permanent magnet. Alternatively or in addition, the guiding element may have a substantially H-shaped longitudinal section with a cross web disposed perpendicular to the axis of rotation and cup-shaped recesses formed on both sides, wherein a permanent magnet is received and non-rotatably connected in one of these recesses. This means that the guiding element may comprise a hollow cylindrical jacket and preferably be configured with an intermediate base arranged substantially at half height of the jacket.

A particularly high concentration of magnetic field lines within the guiding element of the magnetic coupling may be achieved if a diamagnetic or paramagnetic shielding element is arranged at a rear side of the permanent magnet non-rotatably connected to the guiding element, which rear side is facing away from the opposite permanent magnet. In this way, field lines running outside of the coupling parts, in particular outside of the guiding element, may be avoided and thus losses related thereto may be reduced. This means that the "shielding" obtained by the shielding element preferably consists in the magnetic field lines preferably passing through the guiding element rather than through the shielding element.

Furthermore, it has proven favourable in the magnet coupling if a diamagnetic or paramagnetic shielding element is arranged at a front side of the permanent magnet non-rotatably connected to the guiding element, which front side is facing the opposite permanent magnet, in particular in a region centred around the axis of rotation, which shielding element adjoins the guiding element preferably circumferentially or radially on the outside. Such a shielding makes it possible to guide the magnetic field to regions located at larger radial distances from the axis of rotation so the torque transmitted at a given magnetic force is increased.

For preventing a passing over of the carrier medium into the blood in a reliable manner, it is also favourable for the two coupling parts to be hermetically separated. Such a hermetic separation may be obtained, for example, by a hermetic separating wall arranged between the two coupling parts, which wall separates the drive unit and the blood pump hermetically from one another. The hermetic separating wall should be non-conductive both magnetically and electrically. In particular, at least one of the coupling parts may be accommodated in a substantially non-magnetic and electrically non-conductive housing in order to be able to avoid losses due to a reversal of magnetism of the housing and/or induced eddy currents in the housing.

Preferably, the guiding element may be connected non-rotatably to the drive-side coupling part, wherein at least one flushing duct is provided within a hermetic separating wall between the two coupling parts, which flushing duct connects, during operation, a gap between the front side of the pump-side coupling part and the hermetic separating wall to at least one blood flow outside of the hermetic separating wall, wherein said blood flow may either be a blood flow through the blood inlet or a blood flow upstream of the blood inlet. In this way, the flushing duct connects a blood- and a pump-side part of the coupling to a blood flow outside of the coupling. Inflow to the blood- and the pump-side part of the coupling is accomplished via a sliding contact bearing near the coupling in front of the blood-side magnet or via a bore in the shaft of the pump. This means that a connection to a blood flow outside the coupling is established between the front side of the pump-side coupling part and through the hermetic separating wall while the function of the hermetic separation between blood-carrying and non-blood-carrying parts remains intact. By means of such flushing ducts, dead spaces at an output side ("blood side") within the magnetic coupling may be reduced or avoided in their entirety.

In particular, it has been shown that an integrated support, preferably a rolling contact bearing between a drive-side coupling part and the hermetic separating wall, and a sliding contact bearing support between the hermetic separating wall and the output-side coupling part, are provided. This means that the drive-side coupling part is supported rotatably in a rolling contact bearing opposite the hermetic separating wall and the output-side coupling part is supported rotatably in a sliding contact bearing opposite the hermetic separating wall. Such a support provides for a more stable operation and an increased running smoothness in the region of the coupling when compared to coupling parts without support at the front side, since these are subject, among other things, to the risk of the magnetic cup starting to swing and the torque transmission being interrupted.

The conveying of substance via the membrane is determined by three transport resistances: the blood-side substance transition resistance which is also referred to as concentration polarisation, the substance transport resistance by the membrane and the substance transport resistance into the receiving phase (carrier substance) at the permeate side of the membrane. Due to the substantially laminar flow conditions, the boundary layer thickness and thus the substance transition resistance increase with the length of the flow over the membrane. Due to the material properties of the blood—rheology, low coefficient of diffusion and buffer effect—it is most important to reduce the substance transition resistance at the blood side. This is obtained by: a) increasing the speed of the overflow and thus reducing the boundary layer thickness, b) improving the flow distribution and equalisation of the residence time, c) geometric measures by controlled flow guidance, by the installation of statical turbulence promoters, by the geometrically caused induction of secondary flow phenomena and by targeted interruption of the boundary layer build-up, d) more controlled distributing, merging, mixing and redistributing of the blood onto the membrane. The present invention solves this problem by combining measures a) to d).

For this reason it is particularly advantageous to arrange a diverting member between the blood pump and the at least one blood outlet in the cavity, wherein the diverting member is configured to partially divert in the radial direction a blood flow flowing axially through the cavity and/or the diverting member is configured to induce turbulences in this very blood flow. For example, the diverting member may act as a statical turbulence promoter. The partial diverting of the blood in the direction of a radial flow component and/or the inducing of turbulences in the flow make it possible to improve the exchange with the exchange fluid at the substance exchange membrane.

For example, the diverting member may comprise helical, conical (and/or frustum-conical), arrow-shaped and/or disc-shaped guiding surfaces, which are concentric with respect to a longitudinal axis between the blood pump and the blood outlet.

The diverting member may be supported rotatably within the cavity. It may be freely rotatable or preferably coupled to the pump rotor of the blood pump for a forced rotation of the diverting member.

Preferably, the cavity may comprise at least two blood outlets at different distances from the at least one blood inlet. In particular, a first blood outlet may be provided immediately downstream of the blood pump and a second blood outlet may be provided downstream of the substance exchange membrane. The first blood outlet forms a bypass for the substance exchange membrane. During operation, blood may flow through the first blood outlet, from the cavity and from the substance exchange device to the outside into the surroundings of the substance exchange device, for example a surrounding vessel. Due to the drive by the blood pump, this blood has a higher internal energy than the blood passing by the substance exchange device, so the delivery results in a comparably higher local pressure in the vessel. Such an arrangement of multiple blood outlets may also be provided independently of the use of a turbine as the drive unit and thus independently of the arrangement of the rotor and the stator of a turbine as well. Instead of a turbine, the substance exchange device could, for example, comprise an electric motor as the drive unit for the blood pump.

The invention also relates to a substance exchange device for intracorporeal use in general, comprising a cavity for receiving blood having at least one blood inlet and at least one blood outlet, a substance exchange membrane adjoining the cavity, a supply duct for supplying an exchange fluid to the substance exchange membrane, a blood pump arranged within the cavity and a drive unit for the blood pump, wherein the blood pump is configured to pump blood in a direction from the blood inlet to the blood outlet of the cavity, wherein the drive unit comprises a turbine, which is connected to the supply duct and may be driven by an exchange fluid supplied via the supply duct.

BRIEF DESCRIPTION OF THE DRAWINGS

Below the invention is explained in more detail by means of particularly preferred exemplary embodiments, however without being limited to them, and with reference to the drawings. In the individual drawings.

DETAILED DESCRIPTION OF THE INVENTION

Figure 1:
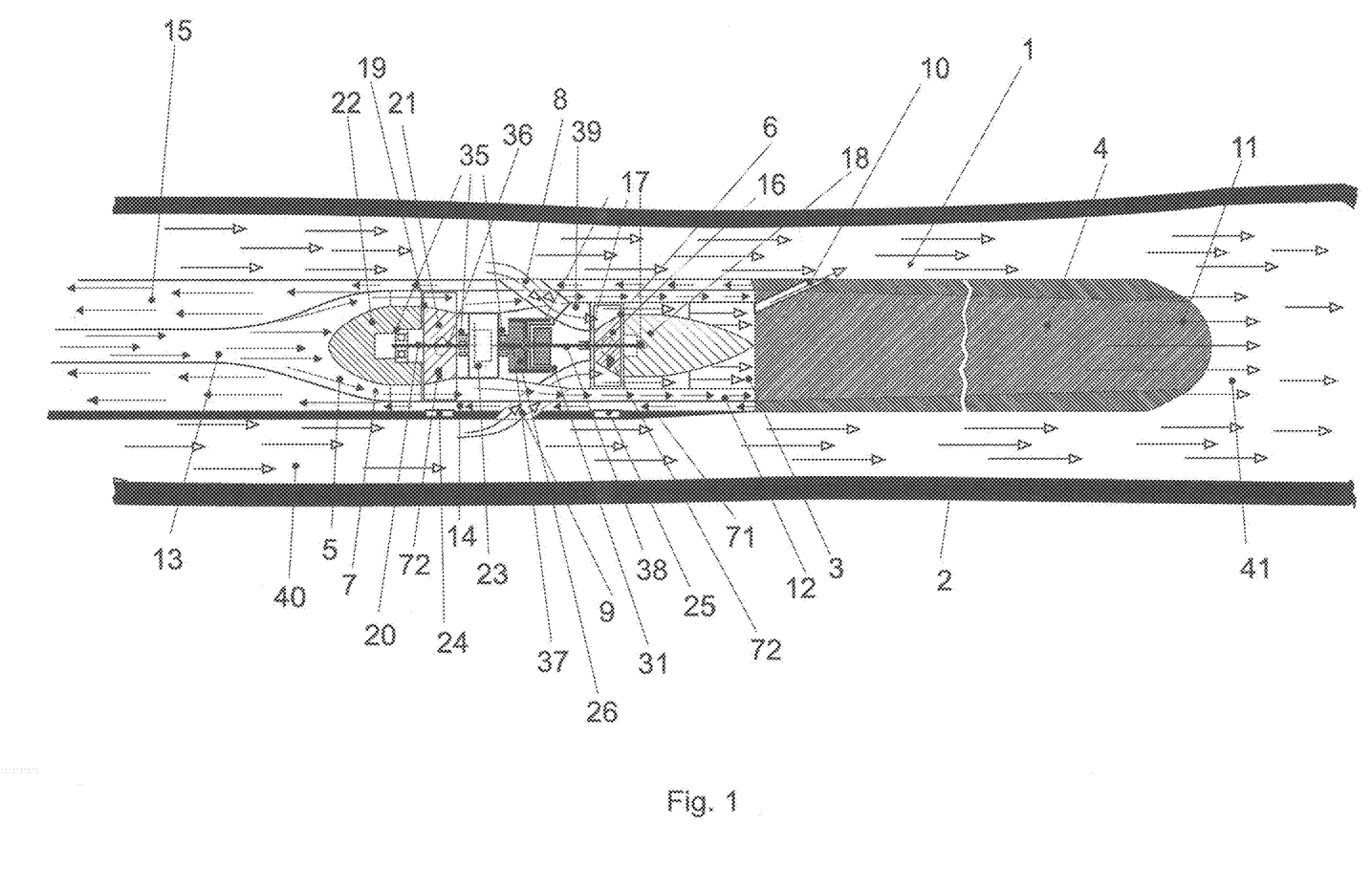
FIG. 1 shows a schematic longitudinal section through a substance exchange device according to the invention during intracorporeal and intravascular use.

FIG. 1 shows a substance exchange device 1 during operation in an intracorporeal arrangement. In this arrangement, the substance exchange device 1 is used as an intravascular catheter in a blood vessel 2. The substance exchange device 1 comprises a cavity 3, a substance exchange membrane 4, a supply duct 5, a blood pump 6 and a drive unit 7. During operation, blood is contained within the cavity 3. The cavity 3 comprises two blood inlets 8, 9 and two blood outlets 10, 11. The two blood outlets 10, 11 are arranged at different distances from the two blood inlets 8, 9. The first blood outlet 10 is arranged immediately downstream of the blood pump 6 and forms a bypass for the substance exchange membrane 4. The second blood outlet 11 is arranged downstream of the substance exchange membrane 4 and forms the proximal end of the substance exchange device 1. The substance exchange membrane 4 adjoins the cavity 3. It may be a hollow-fibre membrane having fibres arranged cylindrically around the cavity 3. The substance exchange membrane 4 keeps a substantially consistent position within the surrounding vessel 2 and is not rotated with respect thereto.

The supply duct 5 is configured to supply an exchange fluid to the substance exchange membrane 4. For example, the exchange fluid may be a low-$CO_2$ gas mixture. The supply duct 5 may connect the inlet 12 of a hollow-fibre membrane to a supply tube 13, which connects the substance exchange device 1 to an extracorporeal transfer device for reconditioning the exchange fluid. Furthermore, the substance exchange device 1 comprises a return duct 14 for returning an exchange fluid from the substance exchange membrane 4. The return duct 14 as well as a return tube 15 connected thereto are configured to withstand a negative pressure. The supply tube 13 and the return tube 15 may be formed as a single multilumen tube, for example a double-walled tube.

The blood pump 6 is arranged within the cavity 3. It is configured to pump blood in a direction from the blood inlets 8, 9 to the blood outlets 10, 11. Preferably, the blood pump 6 is a rotary pump of radial, diagonal or axial design. A pump rotor 16 of the blood pump 6 is supported in at least one sliding contact bearing 17. A diffuser 18 may be arranged downstream of the pump rotor 16 to reduce or entirely remove the rotatory portion of the conveyed medium and convert it to a pressure increase. If this diffuser 18 is not used (for compensating the rotation), however, the flow may also be guided to the substance exchange membrane 4 with a rotation, so the flow does not (only) approach the membrane in the longitudinal direction. The blood pump 6 is arranged for conveying the blood flow in such a way that a sufficient amount of blood flows through the substance exchange membrane 4. In case of intravascular use, the substance exchange device 1 embodies an additional resistance in the vessel 2, which is at least partially compensated by the motion power imparted to the blood by the blood pump 6. At the same time, the pressure loss through the substance exchange device 1 in the vessel 2 may be compensated partially or entirely, or a pressure increase within the vessel 2 may be obtained, depending on the mode of operation. In particular, this may be accomplished by means of the first blood outlet 10, which makes it possible that volumes of blood flowing through the blood pump 6 do not necessarily have to flow through the substance exchange membrane 4 as well.

The drive unit 7 is used for driving the blood pump 6. With its aid, the blood pump may be rotated and thus define the inflow of the blood into the substance exchange membrane 4 with respect to flow direction and volumetric flow. The drive unit 7 comprises a turbine 19. The turbine 19 is connected to the supply duct 5, in particular arranged within the supply duct 5, and may be driven by means of an exchange fluid supplied via the supply duct 5. The turbine 19 comprises a rotor 21, coupled to the blood pump 6 via a rotatably supported shaft 20, and a stator (turbine nozzle) 22 arranged upstream of the rotor 21. The blood pump 6 is coupled to the turbine 19 via a gearing 23. The gearing 23 is configured to reduce the speed of the blood pump 6 with respect to the speed of the turbine 19. It may be a planetary gearing, for example. The drive unit 7 and the blood pump 6 together form a conveying device for conveying blood through the cavity 3 of the substance exchange device 1. During operation, the pump rotor 16 of the blood pump 6 is driven by the turbine 19 in such a way that an acceleration of the blood flow in the region of the blood inlets 8, 9 and thus an overpressure at the distal end of the cavity 3 is created. Here, the speed of the turbine 19 may be controlled by the substance flow and/or the volumetric flow of the exchange fluid such that the differential pressure obtained at the pump just compensates all occurring pressure losses from the blood inlets (8, 9) to the proximal blood outlet (11). This results in an effective compensation of the flow resistance inside the substance exchange device 1 caused by the substance exchange membrane 4.

Two speed sensors 24, 25 are integrated into the substance exchange device 1. The first speed sensor 24 is configured to sense the speed of the turbine 19, the second speed sensor 25 is configured to sense the speed of the blood pump 6. Both speed sensors 24, 25 are Hall sensors. The speed sensors 24, 25 are integrated into a housing 71 of the substance exchange device 1, which surrounds the drive unit 7 and the blood pump 6. As a signal transmitter for the speed sensors 24, 25, a magnet 72 is arranged in each of the rotor 21 of the turbine 19 and the pump rotor 16 of the blood pump 6, preferably centrically (the eccentric illustration is schematically and for easier visibility only; in practice, unbalance is to be avoided).

Figure 7:
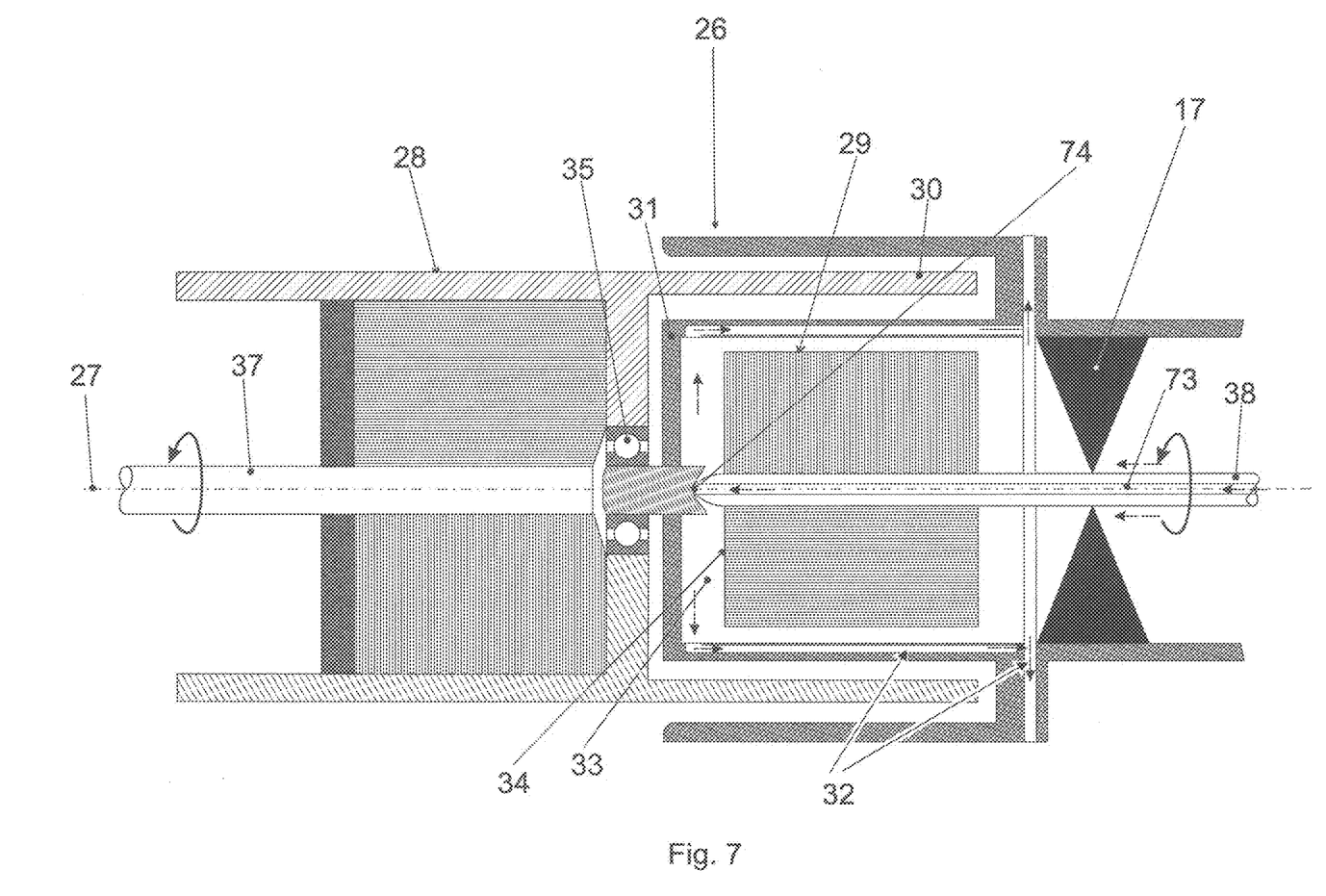
FIG. 7 shows a schematic detail view of the magnetic coupling of the substance exchange device according to FIG. 1.

A pump rotor 16 of the blood pump 6 is coupled to the turbine 19 via a magnetic coupling 26 (cf. FIG. 7). For torque transmission along an axis of rotation 27, the magnet coupling 26 comprises two coupling parts 28, 29 which can be rotated relative to each other, each comprising a two-pole permanent magnet. One of the coupling parts 28 comprises an at least partially ferromagnetic, cup-shaped guiding element 30. The guiding element 30 is non-rotatably connected to the permanent magnet of the drive-side coupling part 28. A part of the guiding element 30 is located radially outside of the permanent magnet of the other coupling part 29. The jacket of the guiding element 30 is only interrupted by a diamagnetic or para-magnetic separation (not illustrated) in a narrow angular region. The diamagnetic separation parts the guiding element 30 substantially into two ferromagnetic halves or half-shells. An intersecting plane running through the diamagnetic or paramagnetic separation is thus perpendicular to a direction of magnetisation of the drive-side two-pole permanent magnet that is connected to the guiding element 30. Consequently, the ferromagnetic sections of the guiding element 30 defined by the diamagnetic or paramagnetic separation are magnetised in accordance with the drive-side permanent magnet.

Due to the contact-free coupling, a hermetic separating wall 31 is provided between the drive-side coupling part 28 and the output-side coupling part 29. At least one flushing duct 32 is provided within the hermetic separating wall 31. The flushing ducts 32 connect a gap 33 between the front side 34 of the pump-side coupling part 29 and the hermetic separating wall 31 to a region adjoining the blood inlets 8, 9. An additional flushing duct 73 is provided within the pump-side shaft section 38 for lubricating a fixed sliding contact bearing cup 74, in which the shaft section 38 is supported. As can be seen in detail in FIG. 7, the rotatable components of the substance exchange device at the output side (also pump side or "blood side") are supported in sliding contact bearings 17, and the rotatable components of the substance exchange device at the drive side (also turbine side) are supported in rolling contact bearings 35 (cf. also FIG. 1).

During operation, a torque is applied to the rotor 21 via the blades of the turbine 19 by the flow of the supplied exchange fluid. The turbine 19 transmits the torque via the shaft 36, which is rotatably supported in rolling contact bearings 35, to the drive side of the gearing 23. At the output side of the gearing 23, a correspondingly higher torque with lower speed is transmitted to the drive-side coupling part 28 of the magnetic coupling 26 via a further shaft section 37. If the drive fluid is a liquid medium, the gearing 23 may be omitted, provided that the turbine and the pump have the same speed at their individual adapted operating points and the torque delivered by the turbine corresponds to the required input torque of the pump. Due to the magnetic forces between the coupling parts 28, 29, the torque is transmitted from the drive-side coupling part 28 to the output-side coupling part 29, wherein the strength of the magnetic forces defines a certain transmittable maximum torque beyond which the coupling parts 28, 29 will "slip" with respect to one another. The output-side coupling part 29 transmits a torque exerted by the drive-side coupling part 28 via a third shaft section 38, which is supported in sliding contact bearings 17, to the pump rotor 16 of the blood pump 6. The pump rotor 16 conveys the blood 40, which approaches through an (optional) flow straightener 39, from the blood inlets 8, 9 through the cavity 3 towards the substance exchange membrane 4 of the substance exchange device 1. In this way, the conveying device creates a pressure difference between the blood inlets 8, 9 and the proximal end of the cavity 3, which pressure difference preferably compensates, substantially entirely, a pressure loss between the proximal and the distal end of the substance exchange device 1 due to the flow resistance of the substance exchange membrane 4, so the blood 41 flowing in the vessel 2 after the substance exchange device 1 has at least the same internal energy as the blood 40 before. The concentration of a substance may have experienced a reduction (e. g. $CO_2$ reduction) or an increase (e.g. $O_2$ enrichment) at the location in the blood 40 to the location in the blood 41.

Instead of a hollow-fibre membrane a different type of membrane may also be used as the substance exchange membrane 4 in the substance exchange device 1, wherein those skilled in the art will adjust the conveying device including the drive unit 7 and the blood pump 6 to the expected pressure difference due to the different flow resistances of other types of membrane.

Figure 2:
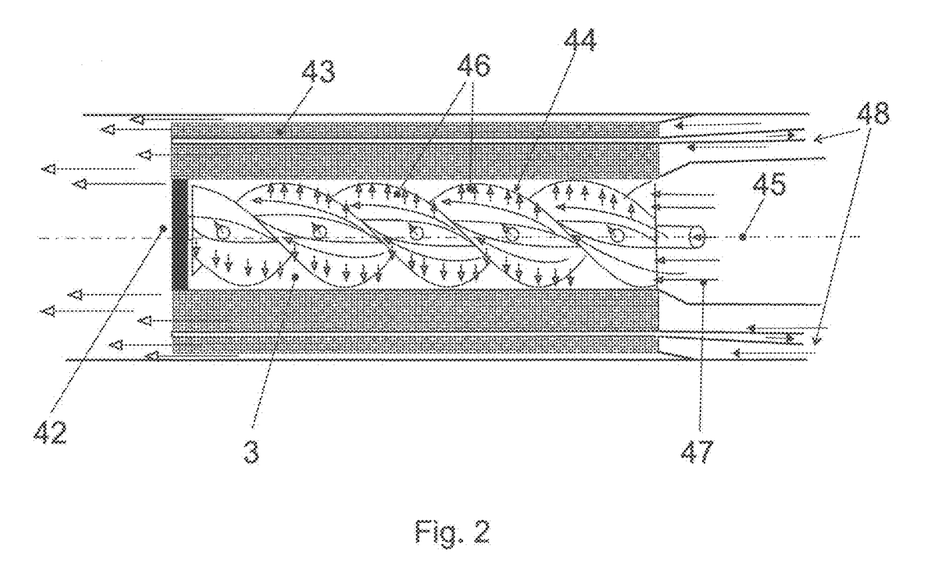
FIG. 2 shows a schematic substance exchange device having a diverting member including helical guiding surfaces.

In the section of an exemplary embodiment shown in FIG. 2, a diverting member 44 is arranged inside a substance exchange membrane 43 between the blood pump (on the right-hand side, not illustrated here) and a blood outlet 42 in the cavity 3. The diverting member 44 is configured to partially divert in the radial direction a blood flow flowing axially through the cavity 3. The diverting member 44 schematically illustrated in FIG. 2 comprises helical guiding surfaces 46 concentric to a longitudinal axis 45 between the blood pump and the blood outlet 42. The diverting member 44 may be fixed rigidly within the cavity 3 of the substance exchange device 1 or supported rotatably within the cavity 3. By means of the helical guiding surfaces 46, the blood 47 approaching from the pump during operation is forced along the longitudinal axis 45 in the centre, constantly radially through the helix over its length and transversely to the substance exchange membrane 43 due to the helical shape. In the substance exchange membrane 43, a mass exchange with an exchange fluid takes place, which exchange fluid is supplied to the substance exchange membrane 43 and/or returned from the substance exchange membrane 43 by supply and return ducts 48.

Figure 3:
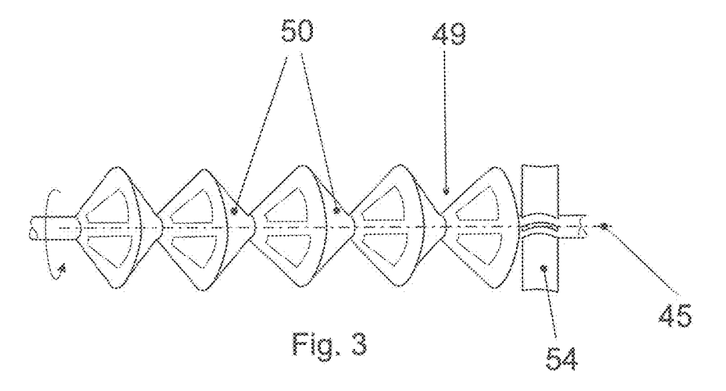
FIG. 3 shows a schematic substance exchange device having a diverting member including frustum-conical guiding surfaces.
Figure 4:
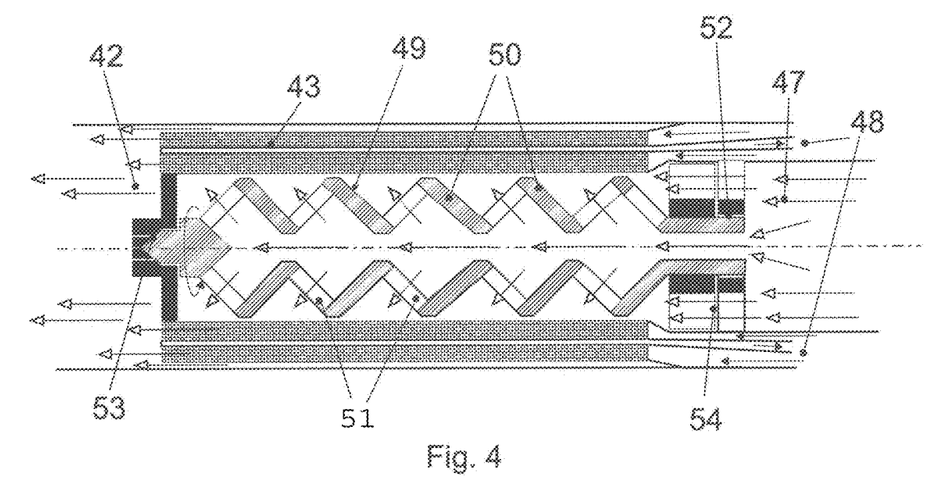
FIG. 4 shows a schematic partial longitudinal section through a substance exchange device having a diverting member according to FIG. 3.

In FIGS. 3 and 4, a further variation of a diverting member 49 is illustrated schematically. The substance exchange membrane 43 as well as the supply and return ducts 48 are the same as those in FIG. 2. The diverting member 49 according to FIGS. 3 and 4 comprises frustum-conical guiding surfaces 50 concentric to a longitudinal axis 45 between the blood pump (not illustrated; right-hand side in FIG. 4) and the blood outlet 42. The blood 47 approaching from the pump during operation flows along the outside of the guiding surfaces 50 through the clearances or holes 51 of the diverting member 49 left open therebetween and through the substance exchange membrane 43. The diverting member 49 is supported freely rotatable between two sliding contact bearings 52, 53. The sliding contact bearing 53 arranged downstream comprises flushing ducts for ensuring lubrication in the region of the bearings. Furthermore, the diverting member 49 comprises a turbine element 54 of its own, which is driven by the blood 47 approaching from the blood pump and thus rotates the diverting member 49. The centrifugal force caused by the rotation effects an additional acceleration of the blood flow in the radial direction through the substance exchange membrane 43 arranged radially outside. A part of the blood flows in the centre of the diverting member 49, which is continuously hollow on its inside, along the longitudinal axis 45.

Figure 5:
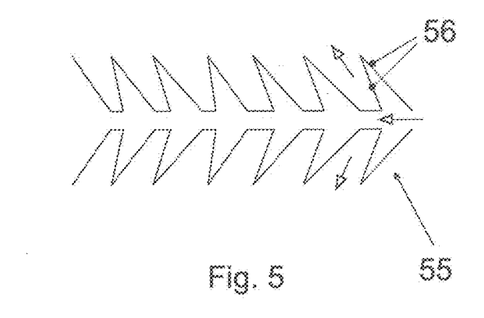
FIG. 5 shows a schematic longitudinal section of a diverting member including arrow-shaped guiding surfaces for use in a substance exchange device according to the invention.
Figure 6:
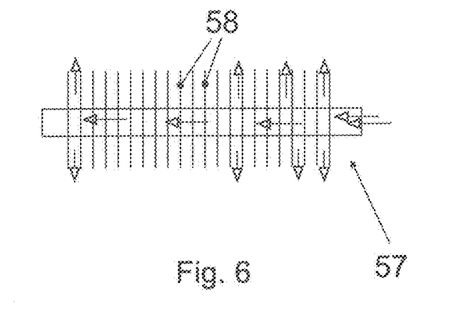
FIG. 6 shows a schematic longitudinal section of a diverting member including disc-shaped guiding surfaces for use in a substance exchange device according to the invention.

FIG. 5 shows, highly simplified, a diverting member 55 with similar operation having arrow-shaped guiding surfaces, and FIG. 6 shows, highly simplified as well, a diverting member 56 having disc-shaped guiding surfaces. The diverting members 44, 49, 55, 57 may each be freely rotatable or optionally be non-rotatably coupled to the pump rotor 16 of the blood pump 6 to co-rotate at the same speed in order to obtain, via a centrifugal force caused by the rotation, an acceleration of the blood flow in the radial direction through a substance exchange membrane 43 arranged radially outside. As an alternative to the coupling to the pump rotor 16, a turbine element 54 (cf. FIG. 4) may be integrated into the respective diverting members.

Figure 8:
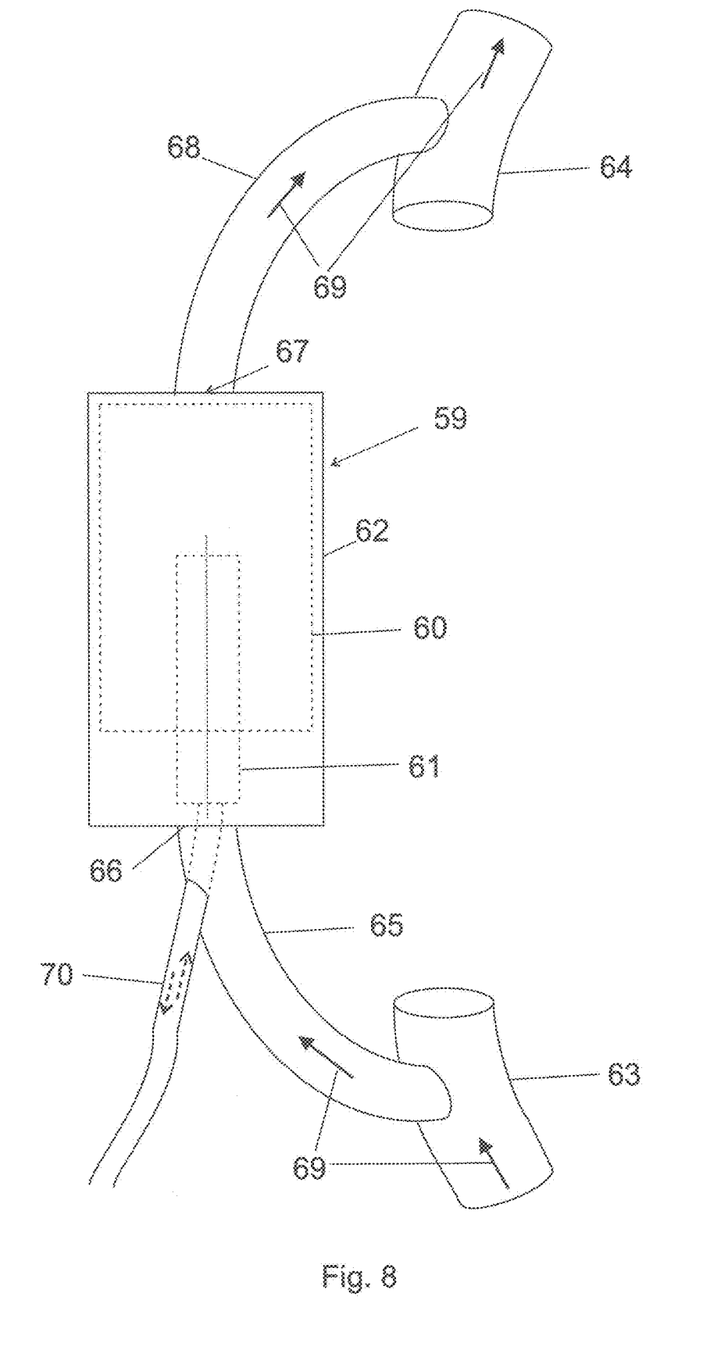
FIG. 8 shows a schematic intracorporeal and extravascular use of a substance exchange device according to the invention.

In the use shown in FIG. 8, a substance exchange device 59 according to the invention (only indicated schematically) having a substance exchange membrane 60 and a conveying device 61 is arranged within a tube 62 foreign to the body, which interconnects two blood vessels 63, 64. A part of the blood flow or the entire blood flow is taken from the first blood vessel 63 through a first tube section 65 and supplied, via a blood inlet 66 of the substance exchange device 59, to the conveying device 61 having a turbine, a magnetic coupling and a blood pump and the substance exchange membrane 60 of the substance exchange device 59. From the blood outlet 67 of the substance exchange device 59, the blood is supplied to the second blood vessel 64 through a second tube section 68. The second blood vessel 64 may be identical to the first blood vessel 63. The flow direction of the blood is indicated by arrows 69. An exchange fluid is supplied to the substance exchange device 59 and returned from the substance exchange device 59 through a multi-lumen tube 70. In this use, a gearing between the turbine and the blood pump may be omitted since when using a gas as the drive fluid for the turbine, the turbine may be configured correspondingly larger due to the spatial conditions. Provided that the turbine and the pump have the same speed at their individual adapted operating points and the torque delivered by the turbine corresponds to the required input torque of the pump.

Figure 9:
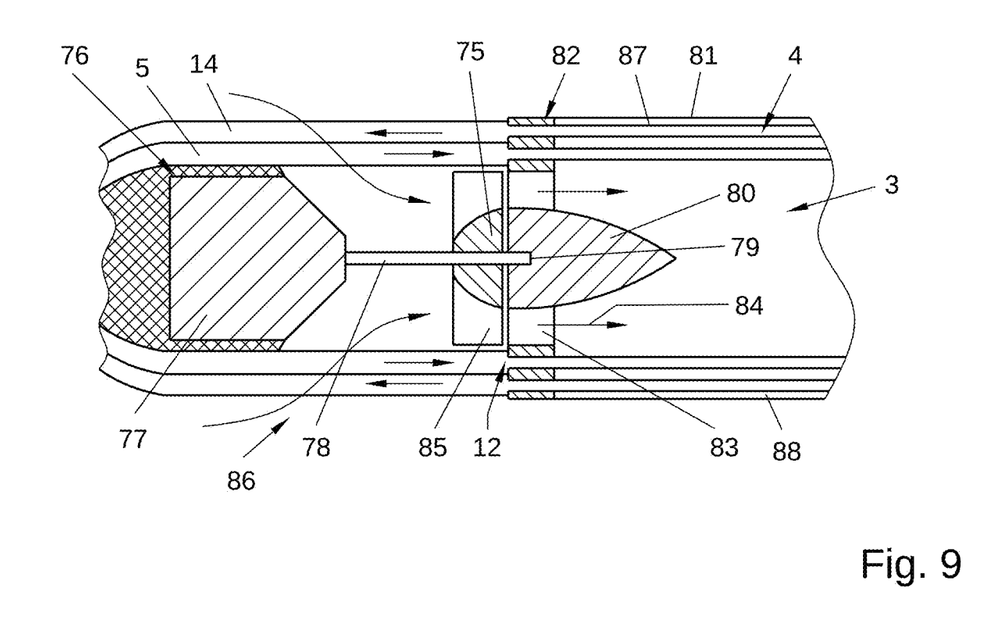
FIG. 9 schematically shows a longitudinal section through a device with an intravascular catheter having a central blood passage and laterally arranged hollow fibre membranes without a proximal reflux lumen and with a motor-driven conveying device at the distal end of the blood passage.

The conveying device represented in FIG. 9 comprises a pump rotor 75 and a drive unit 76 in the form of an electric motor 77. During operation, the electric motor 77 transmits a torque via a shaft 78 to the pump rotor 75. The shaft 78 is supported by means of an end 79 lying opposite the electric motor 77 in a stator 80. The stator 80 is fastened in the catheter 81 in a connecting area 82 via wings 83. Here, the wings 83 are arranged substantially in parallel or slightly angled to a flow direction (indicated by the direction arrows 84) of the blood entering through the lateral blood inlets (not shown) into the catheter 81. The pump rotor 75 itself also has blades 85 which are arranged propeller-like for the axial transport of the blood located between the blades 85 during a rotation of the pump rotor 75.

During operation, the pump rotor 75 is driven by the electric motor 77—which forms a drive unit—in such a way that an acceleration of the blood flow in the area of the blood inlets and, thus, an excess pressure at the distal end 86 of the catheter 81 are generated. In this connection, the rotational speed of the electric motor 77 is controlled via a control (not shown) such that the obtained excess pressure just compensates for a pressure difference between the blood inlets and the blood outlet 11 (see FIG. 1). Thereby the flow resistance caused by the hollow fibres 87, 88 inside the catheter 81 is effectively compensated for.

Figure 10:
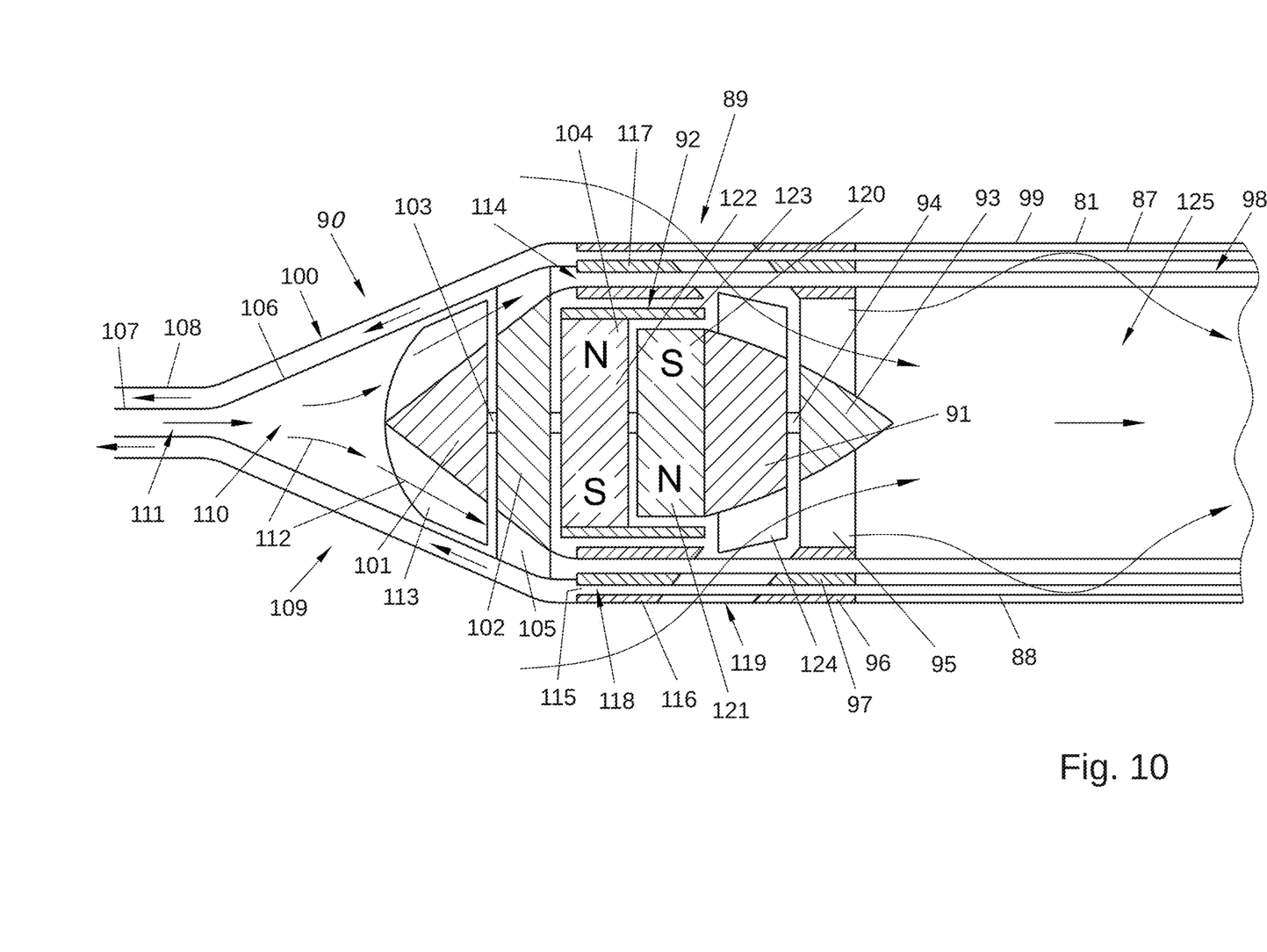
FIG. 10 schematically shows a longitudinal section through a device with an intravascular catheter having

FIG. 10 shows a further, preferred embodiment for a conveying device 89. The conveying device 89 forms the distal end 90 of the catheter 81. The conveying device 89 comprises a pump rotor 91 which is rotatably arranged between a magnetic coupling 92 and a pump stator 93 and is rotatably supported with a shaft 94 in the pump stator 93. The pump stator 93 is fastened via lateral wings 95 in a first connecting ring 96. The first connecting ring 96 comprises an embedding mass 97 in which the hollow fibres 87, 88 of the hollow fibre membrane 98 are embedded and with which they are connected, wherein the hollow fibres 87, 88 extend through the first connecting ring 96 axially, i.e. in parallel to a longitudinal axis of the catheter 81. The first connecting ring 96 is connected at a radial outer side to the catheter tube 99 of the catheter 81.

The conveying device 89 further comprises as a drive unit 100 a turbine element 101 which is supported in a turbine stator 102 such that it is rotatable around a shaft 103. The shaft 103 forms a non-rotatable connection of the turbine element 101 with the magnetic coupling 92, in particular with a drive-side coupling part 104. The turbine stator 102 is arranged between the drive-side coupling part 104 and the turbine element 101 which acts as a turbine rotor, wherein the shaft 103 extends through the turbine stator 102. The turbine stator 102 has lateral wings 105 by means of which it is fastened in a section 106 of the inner tube 107 of a feeding tube 108, said section 106 being widened in the connecting area 109. Correspondingly, the turbine element 101 is also arranged in the widened section 106, and, thus, it is subjected to the flow of a carrier liquid 110 supplied through a supply channel 111 of the feeding tube 108. As is indicated by the direction arrows 112, the flow of the carrier liquid 110 leads out of the supply channel 111 into the widened section 106 via propeller-like blades 113 arranged at the turbine element 101 for the reception of a torque and past the wings 105 of the turbine stator 102 to the inlet 114 of the hollow fibre membrane 98.

The ring-shaped inlet 114 and outlet 115 of the hollow fibre membrane 98 is formed at a second connecting ring 116 which comprises an embedding mass 117 in which the ends 118 of the hollow fibres 87, 88 are embedded so that they lead into the inlet 114 or into the outlet 115. Between the second connecting ring 116 and the first connecting ring 96 which is arranged proximal of the second connecting ring 116, the catheter 81 has lateral blood inlets 119.

Apart from the drive-side coupling part 104, the magnetic coupling 92 also comprises a corresponding output-side coupling part 120 which is non-rotatably connected to the pump rotor 91. Due to the rotatable support via the separated shafts 94, 103 in the stators 93, 102, the drive-side coupling part 104 is rotatably supported relative to the output-side coupling part 120. The output-side coupling part 120 comprises an output-side two-pole permanent magnet 121 which is non-rotatably connected to the shaft 94 of the pump rotor 91. The drive-side coupling part 104 comprises a drive-side two-pole permanent magnet 122 which is non-rotatably connected to the shaft 103 of the turbine element 101. The output-side permanent magnet 121 is circumferentially surrounded by a substantially cup-shaped guiding element 123 having a hollow cylindrical jacket. In this connection, there is provided a clearance or gap between the output-side permanent magnet 121 and the guiding element 123 so that the output-side coupling part 120 is coupled to the drive-side coupling part 104 in a contact-free fashion. The guiding element 123 is mainly made of a ferromagnetic material. The jacket of the guiding element 123 is interrupted by a diamagnetic separation (not shown) only in a narrow angular region. Substantially, the separation parts the guiding element 123 into two ferromagnetic halves or half-shells. An intersecting plane running through the separation is thus perpendicular to a direction of magnetisation of the drive-side two-pole permanent magnet 122 that is connected to the guiding element 123. Consequently, the ferromagnetic sections of the guiding element 123 defined by the separation are magnetised in accordance with the drive-side permanent magnet 122.

Due to the contact-free coupling there is provided a hermetic separation (not shown) between the drive-side coupling part 104 and the output-side coupling part 120. The hermetic separation is formed by a foil sealingly connected with the radial inner side of the second connecting ring 116.

During operation, by the flow of the supplied carrier liquid a torque is applied via the blades 113 to the turbine element 101. The turbine element 101 transmits the torque via the shaft 103 to the drive-side coupling part 104 of the magnetic coupling 92. By the magnetic forces between the coupling parts 104, 120, the torque is transmitted from the drive-side coupling part 104 to the output-side coupling part 120, wherein the power of the magnetic forces defines a certain maximum transmittable torque beyond which a "slipping" of the coupling parts 104, 120 relative to each other occurs. The output-side coupling part 120 transmits a torque exerted by the drive-side coupling part 104 via the shaft 94 to the pump rotor 91. By means of lateral propeller-like blades 124, the pump rotor 91 transports the blood located between the blades 124 from the blood inlets 119 in the direction of the blood passage 125 inside the catheter 81. In this way, the conveying device 89 generates a pressure difference between the blood inlets 119 and the proximal end of the blood passage 125 which preferably and substantially completely compensates for a pressure difference between the proximal and the distal end (not shown) of the catheter 81 which is due to the flow resistance of the hollow fibre membrane 98. Here, the turbine element 101 and the pump rotor 91 are preferably tuned with each other.

While the invention has been described in connection with what is presently considered to be the most practical and preferred embodiments, it is to be understood that the invention is not to be limited to the disclosed embodiments, but on the contrary, is intended to cover various modifications and equivalent arrangements included within the spirit and scope of the appended claims.

The invention claimed is:

1. A substance exchange device for intracorporal use, comprising:
    a cavity for receiving blood having at least one blood inlet and at least one blood outlet,
    a substance exchange membrane adjoining the cavity,
    a supply duct for supplying an exchange fluid to the substance exchange membrane,
    a blood pump arranged within the cavity and
    a drive unit for the blood pump,
    wherein the blood pump is configured to pump blood in a direction from a blood inlet to a blood outlet of the cavity,
    wherein the drive unit comprises a turbine, which is connected to the supply duct and may be driven by an exchange fluid supplied via the supply duct, and
    wherein the turbine comprises at least a rotor coupled to the blood pump and a stator.

2. The substance exchange device according to claim 1, wherein the stator of the turbine is arranged upstream of the rotor of the turbine.

3. The substance exchange device according to claim 1, wherein a pump rotor of the blood pump is supported in a sliding contact bearing.

4. The substance exchange device according to claim 1, wherein at least one speed sensor is integrated with the substance exchange device, which speed sensor is configured to sense the speed of the turbine, the blood pump or a coupling between the blood pump and the turbine.

5. The substance exchange device according to claim 1, wherein the blood pump is coupled to the turbine via a gearing, wherein the gearing is configured to reduce the speed of the blood pump with respect to the speed of the turbine.

6. The substance exchange device according to claim 1, comprising a return duct for returning an exchange fluid from the substance exchange membrane and/or the turbine, wherein the return duct is configured to withstand a negative pressure.

7. The substance exchange device according to claim 1, wherein a pump rotor of the blood pump is connected to the turbine via a magnetic coupling, wherein the magnetic coupling comprises two coupling parts for torque transmission along an axis of rotation, said coupling parts being rotatable relative to each other and each having a permanent magnet.

8. The substance exchange device according to claim 7, wherein one of the coupling parts comprises an at least partially ferromagnetic guiding element which is non-rotatably connected to the permanent magnet of the coupling part, wherein one part of the guiding element is disposed radially outside of the permanent magnet of the other coupling part.

9. The substance exchange device according to claim 8, wherein the at least partially ferromagnetic guiding element comprises at least one diamagnetic or paramagnetic separation.

10. The substance exchange device according to claim 7, wherein between the two coupling parts a hermetic separating wall is arranged, which separates the drive unit and the blood pump hermetically from one another.

11. The substance exchange device according to claim 10, wherein an integrated bearing between a drive-side coupling part and the hermetic separating wall, and a sliding contact bearing between the hermetic separating wall and the output-side coupling part are provided.

12. The substance exchange device according to claim 11, wherein said integrated bearing is a rolling contact bearing.

13. The substance exchange device according to claim 8, wherein the guiding element is non-rotatably connected to the drive-side coupling part, wherein within a hermetic separating wall between the two coupling parts at least one flushing duct is provided, which connects, during operation, a gap between the front side of the pump-side coupling part and the hermetic separating wall to at least one blood flow outside of the hermetic separating wall, wherein said blood flow may be either a blood flow through the blood inlet or a blood flow upstream of the blood inlet.

14. The substance exchange device according to claim 1, wherein between the blood pump and the at least one blood outlet in the cavity a diverting member is arranged, wherein the diverting member is configured to partially divert in the radial direction a blood flow flowing axially through the cavity and/or to induce turbulences in this very blood flow.

15. The substance exchange device according to claim 14, wherein the diverting member comprises helical, conical, arrow-shaped and/or disc-shaped guiding surfaces, which are concentric with respect to a longitudinal axis between the blood pump and the blood outlet.

16. The substance exchange device according to claim 14, wherein the diverting member is supported rotatably within the cavity.

17. The substance exchange device according to claim 1, wherein the cavity comprises at least two blood outlets at different distances from the at least one blood inlet.

* * * * *